United States Patent
Link et al.

(10) Patent No.: US 12,099,652 B1
(45) Date of Patent: Sep. 24, 2024

(54) DETERMINING IPD BY ADJUSTING THE POSITIONS OF DISPLAYED STIMULI

(71) Applicant: Microsoft Technology Licensing, LLC, Redmond, WA (US)

(72) Inventors: Gregory Michael Link, Charlotte, NC (US); Michaela Porubanova, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/243,030

(22) Filed: Sep. 6, 2023

(51) Int. Cl.
*G06F 3/01* (2006.01)
*G09G 3/00* (2006.01)

(52) U.S. Cl.
CPC ............ *G06F 3/013* (2013.01); *G09G 3/001* (2013.01); *G09G 2340/0464* (2013.01); *G09G 2354/00* (2013.01)

(58) Field of Classification Search
CPC ........... G09G 3/001; G09G 2340/0464; G09G 2354/00; G06V 40/19
USPC ............................................................. 345/8
See application file for complete search history.

(56) References Cited

U.S. PATENT DOCUMENTS

2016/0065952 A1* 3/2016 Han ...................... G06V 40/19
345/8

* cited by examiner

*Primary Examiner* — Abdul-Samad A Adediran
(74) *Attorney, Agent, or Firm* — Workman Nydegger

(57) ABSTRACT

Techniques for determining a user's IPD are described. A first stimulus is displayed on a first display, and a second stimulus is displayed on a second display. A stimulus separation distance is a distance that exists between the first and second stimuli. The stimulus separation distance is progressively increased by progressively moving, in opposing directions relative to one another, the first and second stimuli. While that distance is being progressively increased, at least one of the user's eyes is tracked. While the distance is being progressively increased, a change in a rate of eye movement for the user's eye is detected. When the change is detected, a value for the stimulus separation distance is recorded. The recorded value is set as a baseline for the user's IPD.

20 Claims, 14 Drawing Sheets

DETERMINING IPD BY ADJUSTING THE POSITIONS OF DISPLAYED STIMULI

BACKGROUND

The phrase "extended reality" (ER) is an umbrella term that collectively describes various types of immersive platforms. Such immersive platforms include virtual reality (VR) platforms, mixed reality (MR) platforms, and augmented reality (AR) platforms.

For reference, conventional VR systems create completely immersive experiences by restricting their users' views to only virtual environments. This is often achieved through the use of a head mounted device (HMD) that completely blocks any view of the real world. With this HMD, a user can be entirely or partially immersed within an immersive environment. Conventional AR systems create an augmented reality experience by visually presenting virtual objects that are placed in the real world. Conventional MR systems also create an augmented reality experience by visually presenting virtual objects that are placed in the real world. In the context of an MR system, those virtual objects are typically able to be interacted with by the user, and those virtual objects can interact with real world objects. AR and MR platforms can also be implemented using an HMD.

Unless stated otherwise, the descriptions herein apply equally to all types of ER systems, which include MR systems, VR systems, AR systems, and/or any other similar system capable of displaying virtual content. An ER system can be used to display various types of information to a user. Some of that information is displayed in the form of a "hologram." As used herein, the term "hologram" (aka "stimulus") generally refers to virtual image content that is displayed by an ER system. In some instances, the hologram can have the appearance of being a three-dimensional (3D) object while in other instances the hologram can have the appearance of being a two-dimensional (2D) object.

Often, holograms are displayed in a manner as if they are a part of the actual physical world. For instance, a hologram of a flower vase might be displayed on a real-world table. In this scenario, the hologram can be considered as being "locked" or "anchored" to the real world. Such a hologram can be referred to as a "world-locked" hologram or a "spatially locked" hologram that is spatially anchored to the real world. Regardless of the user's movements, a world-locked hologram will be displayed as if it was anchored or associated with a specific physical space or object in the real-world. Other holograms can be locked to a particular position in the user's field of view (FOV).

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

In some aspects, the techniques described herein relate to a computer system that determines an interpupillary distance (IPD) of a user, said computer system including: a first display; a second display; a processor system; and a storage system that stores instructions that are executable by the processor system to cause the computer system to: display a first stimulus on the first display, the first stimulus being visible to a first eye of the user; display a second stimulus on the second display, the second stimulus being visible to a second eye of the user, wherein a stimulus separation distance is a distance that exists between the first stimulus and the second stimulus; progressively increase the stimulus separation distance by progressively moving, in opposing horizontal directions relative to one another, the first stimulus and the second stimulus; while the stimulus separation distance is being progressively increased by progressively moving the first stimulus and the second stimulus, track at least one of the user's first eye and the user's second eye; while the stimulus separation distance is being progressively increased, detect a change in a rate of eye movement for at least one of the user's first eye and the user's second eye and, when the change in the rate of eye movement is detected, record a value for the stimulus separation distance; and set the recorded value for the stimulus separation distance as a baseline for the user's IPD.

In some aspects, the techniques described herein relate to a method for determining an interpupillary distance (IPD) of a user, said method including: displaying a first stimulus on a first display, the first stimulus being visible to a first eye of the user; displaying a second stimulus on a second display, the second stimulus being visible to a second eye of the user, wherein a stimulus separation distance is a distance that exists between the first stimulus and the second stimulus; progressively increasing the stimulus separation distance by progressively moving, in opposing horizontal directions relative to one another, the first stimulus and the second stimulus; while the stimulus separation distance is being progressively increased by progressively moving the first stimulus and the second stimulus, tracking at least one of the user's first eye and the user's second eye; while the stimulus separation distance is being progressively increased, detecting a change in a rate of eye movement for at least one of the user's first eye and the user's second eye and, when the change in the rate of eye movement is detected, recording a value for the stimulus separation distance; and setting the recorded value for the stimulus separation distance as a baseline for the user's IPD.

In some aspects, the techniques described herein relate to a method for determining an interpupillary distance (IPD) of a user, said method including: displaying a first stimulus on a first display, the first stimulus being visible to a first eye of the user; displaying a second stimulus on a second display, the second stimulus being visible to a second eye of the user, wherein a stimulus separation distance is a distance that exists between the first stimulus and the second stimulus; progressively increasing the stimulus separation distance by progressively moving, in opposing horizontal directions relative to one another, the first stimulus and the second stimulus; while the stimulus separation distance is being progressively increased by progressively moving the first stimulus and the second stimulus, tracking the user's first eye; while the stimulus separation distance is being progressively increased, detecting a change in a rate of eye movement for the user's first eye and, when the change in the rate of eye movement is detected, recording a value for the stimulus separation distance; and setting the recorded value for the stimulus separation distance as a baseline for the user's IPD.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Figure 1:
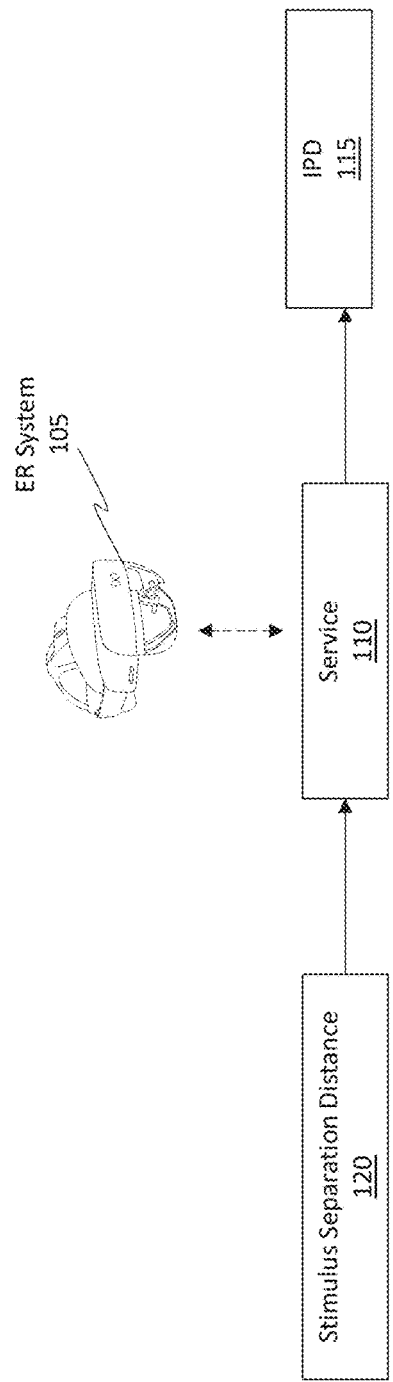
FIG. 1 illustrates an example architecture that can determine a user's IPD.

As mentioned previously, HMDs are capable of displaying holograms (aka "stimuli"). A user can view and interact with these holograms while wearing the HMD.

Often, an HMD will include a lefthand display, which is viewed by the user's left eye, and a righthand display, which is viewed by the user's right eye. In some cases, the lefthand and righthand displays are separate display units. In other cases, the lefthand and righthand displays are part of the same display unit, and the display unit displays content at specific locations to be seen by the user's eyes.

To provide the illusion of depth for a stimulus, the HMD will display one version of a stimulus at a particular horizontal coordinate in the HMD's lefthand display. Another version of the stimulus will be displayed at a different horizontal coordinate in the HMD's righthand display. The disparity or offset in the horizontal pixel locations of the stimulus results in a perception of depth for the stimulus when the user's mind fuses the two display images/stimuli together. The distance between the stimulus as presented in the lefthand display and the stimulus as presented in the righthand display is referred to herein as the "stimulus separation distance."

When an image or stimulus is rendered, it is desirable to render the stimulus from a position that corresponds to the user's eyes. To do so, the HMD provides a synthetic or simulated camera that matches or otherwise closely aligns with the user's pupil position. For instance, the simulated camera can be positioned at the user's center of sight, which may not strictly be the exact location of the user's pupil but that may closely approximate that position. Stated differently, it is generally desirable to position the simulated cameras at the same or sufficiently similar focal points as the user's eyes. This camera generates the content for the user to view and interact with. Deviations between the position of the simulated camera and the position of the user's pupils cause some of the problems mentioned above because the two perspectives are not matched. The phrase "render camera position" refers to a position of a simulated camera, often with reference to the user's pupils. It is desirable to have the render camera position of a simulated camera be as close to the user's pupil as possible. If the render camera position is not accurate, then the stimulus separation distance may also not be correct, leading to depth perception issues. The phrase "render camera separation" refers to the separation distance between the two simulated cameras.

"IPD," or interpupillary distance, refers to the distance between a user's pupils. For an adult, the average IPD ranges between about 54 millimeters (mm) to about 68 mm.

IPD is often used as an input when rendering content with an HMD (e.g., using the simulated cameras). For example, IPD provides information for determining how far apart the simulated cameras should be to enable the HMD to properly render content for the user. If the HMD's IPD parameter is not correctly matched with the user's actual IPD (in other words, if the render camera separation does not correspond with the user's IPD), user comfort as well as user performance are negatively impacted. Particularly problematic is the case where the render camera separation (and also the stimulus separation distance) is larger than the user's IPD. In fact, one severe issue that can arise includes divergent eye movements which force eye muscles to rotate beyond parallel, leading to severe and acute discomfort. Thus, IPD has an impact on the render camera position, and the render camera position has an impact on the stimulus separation distance. Consequently, IPD plays a role in determining the stimulus separation distance.

Often the render camera separation cannot be sufficiently matched or correlated with the user's IPD. This typically happens because eye trackers and eye models are not error-free and thus often do not accurately determine the user's IPD. In many situations, existing eye tracking systems can be erroneous up to about 2 millimeters (mm). If an adult's IPD were on the lower end of the average range (e.g., about 54 mm), then a 2 mm error can result in a percentage error of about 3.7%. Such errors can compromise accurate depth estimation, resulting in inaccurate manipulation with and estimation of virtual objects.

Under-matching the render camera separation to IPD (i.e. setting the render camera separation to be smaller than the user's IPD) is more beneficial with respect to precise fine motor tasks as compared to over-matching (i.e. setting the render camera separation to be larger than the user's IPD). For example, when a user is performing a task that requires perceptual alignment or perceptual matching, tests have shown that under-matching is preferable to over-matching. In fact, setting the render camera separation to be between about 60%-90% of the user's IPD improves precise depth performance while not compromising the user's visual comfort. However, the impact of a larger render camera separation for far viewing tasks is more about comfort than precision. As such, avoiding render camera separations that are larger than the user's IPD is desirable to maintain proper comfort, even for far viewing distances.

The disclosed embodiments are directed to techniques for optimizing or improving how a user's IPD is determined so that a correct render camera position and render camera separation can be determined. Facilitating these improved calculations results in better imagery being generated and displayed to the user. The embodiments thereby optimize or improve the user's experience with respect to viewing tasks.

Generally, the disclosed embodiments present various solutions that help determine the correct IPD by observing smooth pursuit eye movements in response to virtual content moving at a slow speed away from the user. Under normal circumstances, the user will be able to smoothly track the virtual object, eventually resulting in both eyes gazing in parallel as the virtual object asymptotically approaches 0 diopters. If the system's IPD parameter for the user (effectively the render camera separation) is wider than the user's actual IPD, fixating on the virtual object will eventually require the user's eyes to diverge, thereby interrupting the smooth pursuit motion.

The physical distance between the dichoptic content making up the virtual target at the point of interruption of smooth pursuit eye movements (mentioned above) indicates user IPD, and the embodiments are beneficially able to detect that interruption and then determine IPD. In other words, once this interruption of eye pursuit movement is reached, the embodiments are able to detect that interruption and use that event to generate accurate input for the system's IPD parameter, resulting in improved comfort and object location accuracy. Accordingly, these and numerous other benefits will now be described in more detail throughout the remaining portions of this disclosure.

Example Architectures

Figure 2:
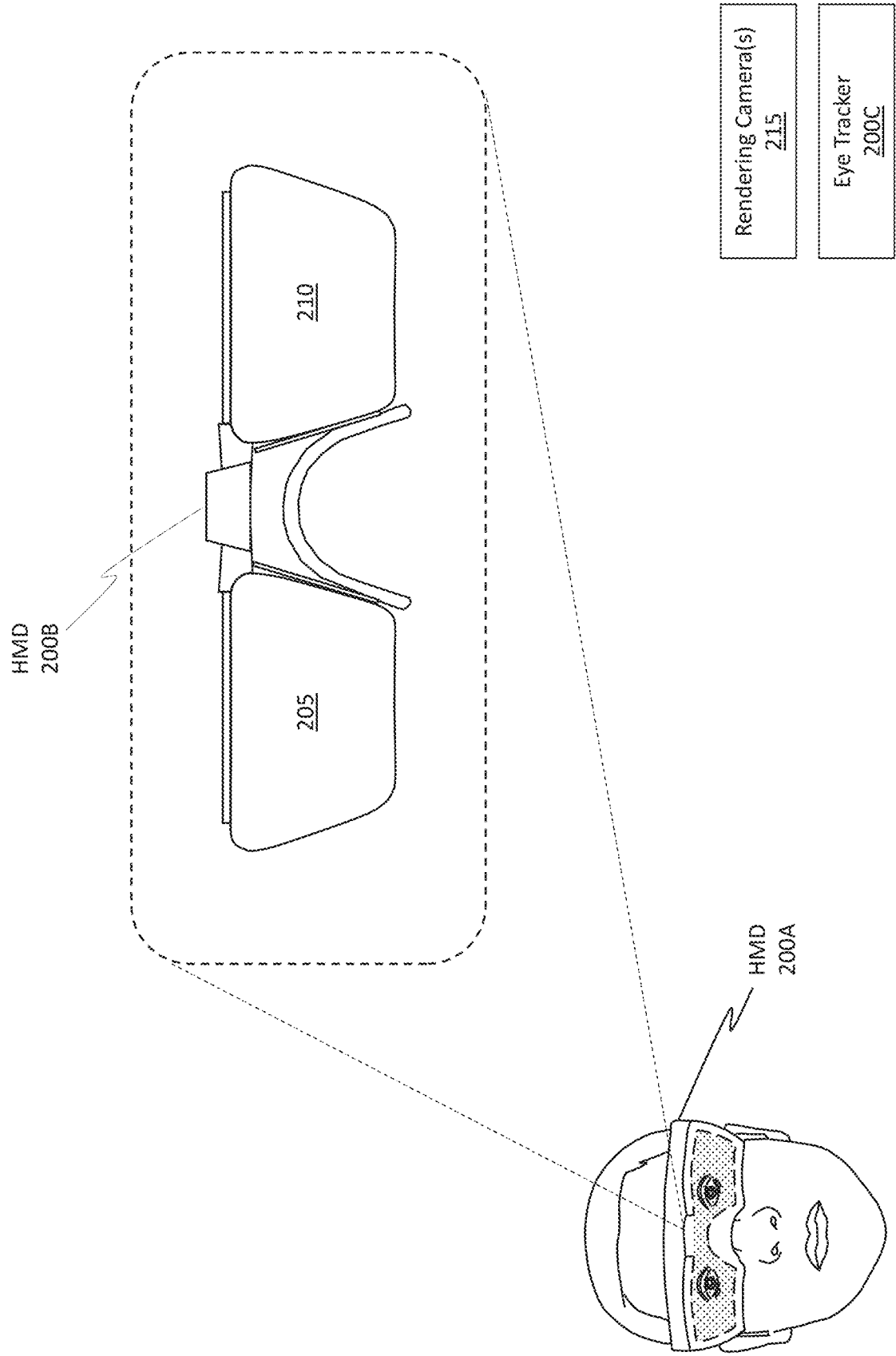
FIG. 2 illustrates an example HMD.

Attention will now be directed to FIG. 1, which illustrates an example architecture 100 that can be used to achieve the benefits, advantages, and practical applications mentioned above. Architecture 100 can, for example, be implemented by an ER system 105, which includes an HMD. As used herein, the phrases ER system and HMD can be used interchangeably and generally refer to a type of system that allows a user to see virtualized content in the form of holograms. ER system 105 can be a VR, AR, or MR system. FIG. 2 provides additional details.

Turning briefly to FIG. 2, FIG. 2 shows an HMD 200A and HMD 200B, which are representative of the ER system 105 of FIG. 1. HMD 200B includes a lefthand display 205 and a righthand display 210. Each display may be associated with a corresponding rendering camera, as shown by rendering camera(s) 215 (i.e. the synthetic or simulated camera mentioned earlier). The rendering camera(s) 215 render or display content on the displays 205 and 210. HMD 200B can also include one or more eye trackers, as shown by eye tracker 200C. It is desirable that the location of these rendering camera(s) 215 matches the user's pupil. Thus, it is desirable that the render camera separation that exists between these rendering camera(s) 215 matches the user's IPD.

Any type of eye tracker 200C may be used. In some scenarios, eye tracker 200C includes a low cost or lower resolution type of eye tracker. For instance, eye tracker 200C may include one or more distance finders directed to the user's pupil(s), one or more electromyograph (EMG) sensors directed to the user's eye(s) (i.e. a sensor that measures muscle or nerve activity), one or more low resolution cameras, one or more non-infrared cameras, or even one or more radio frequency mapping sensors that monitor the user's eyes and that map the eye movement(s) in a single dimension.

Returning to FIG. 1, architecture 100 is shown as including a service 110, which can also be implemented on the ER system 105. As used herein, the term "service" refers to an automated program that is tasked with performing different actions based on input. In some cases, service 110 can be a deterministic service that operates fully given a set of inputs and without a randomization factor. In other cases, service 110 can be or can include a machine learning (ML) or artificial intelligence engine. The ML engine enables service 110 to operate even when faced with a randomization factor.

As used herein, reference to any type of machine learning or artificial intelligence may include any type of machine learning algorithm or device, convolutional neural network(s), multilayer neural network(s), recursive neural network(s), deep neural network(s), decision tree model(s) (e.g., decision trees, random forests, and gradient boosted trees) linear regression model(s), logistic regression model(s), support vector machine(s) ("SVM"), artificial intelligence device(s), or any other type of intelligent computing system. Any amount of training data may be used (and perhaps later refined) to train the machine learning algorithm to dynamically perform the disclosed operations.

In some implementations, service 110 is a cloud service operating in a cloud environment. In some implementations, service 110 is a local service operating on a local device, such as the ER system 105. In some implementations, service 110 is a hybrid service that includes a cloud component operating in the cloud and a local component operating on a local device. These two components can communicate with one another.

Figure 3:
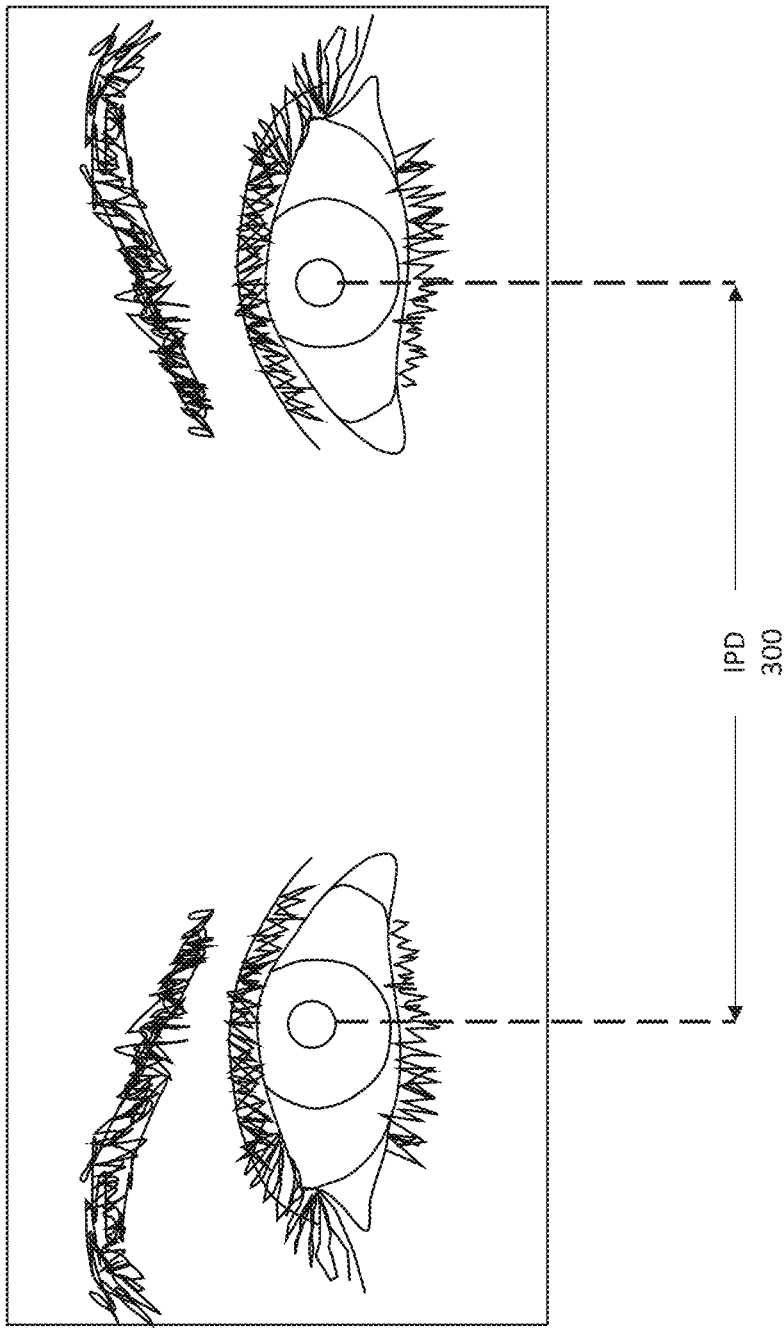
FIG. 3 illustrates an example of a user's IPD.

Service 110 is generally tasked with determining a user's IPD 115. For example, turning briefly to FIG. 3, a user's IPD 300 is shown. IPD 300 is the distance between the user's two pupils. It is desirable to cause the simulated cameras to be positioned immediately in front of the user's pupils, resulting in the render camera separation of the rendering cameras to match the user's IPD 300.

Returning to FIG. 1, service 110 determines the IPD 115 by dynamically modifying the stimulus separation distance 120 that exists between two stimuli that are displayed to a user. This modification occurs until a particular type of interruption in the user's rate of eye movement is detected. FIGS. 4 through 12 are illustrative.

Figure 4:
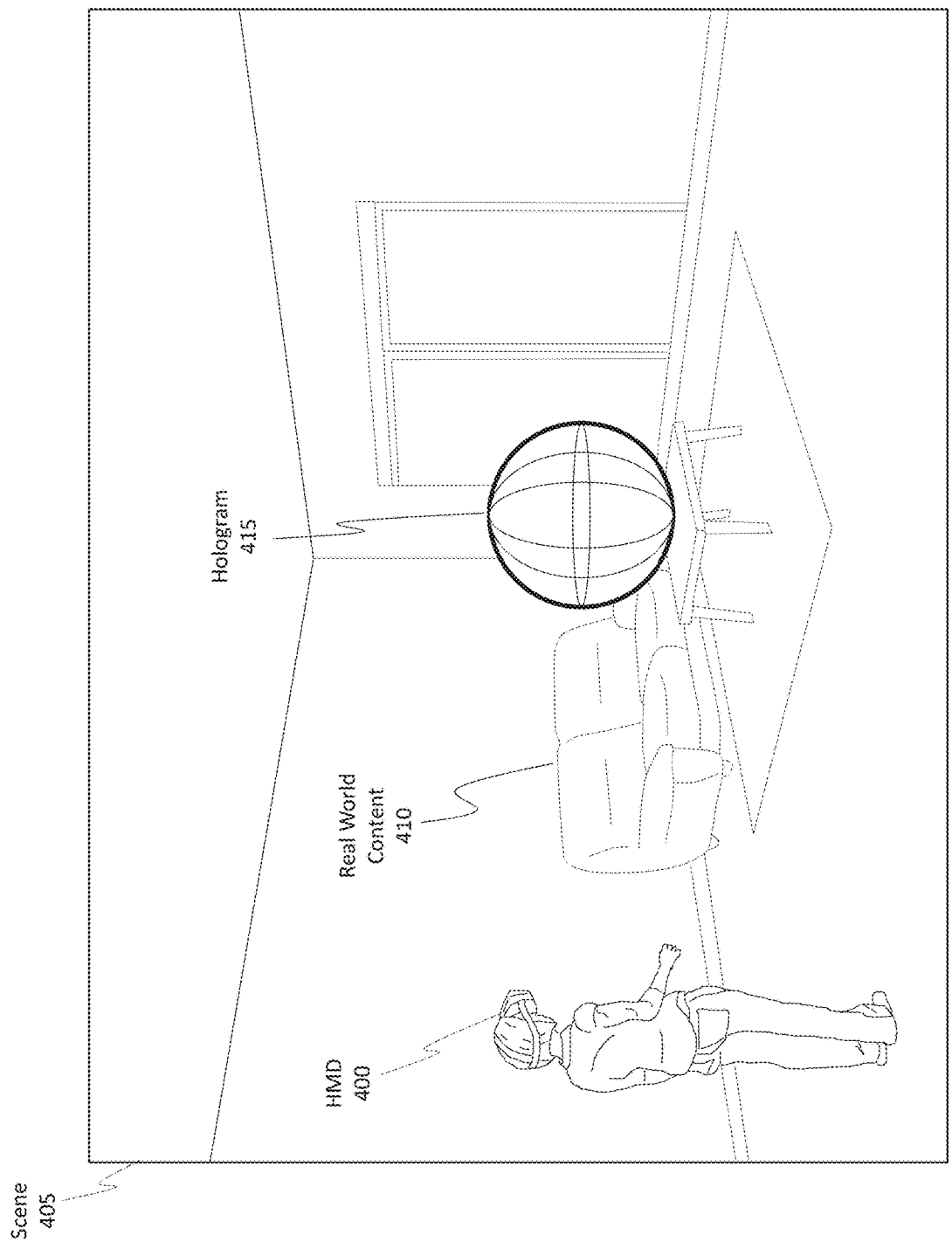
FIG. 4 illustrates a scene rendered by a system.

FIG. 4 shows a scenario in which a user is wearing an HMD 400, which corresponds to the HMD 200B of FIG. 2. HMD 400 is rendering a scene 405 for the user. As used herein, the term "scene" generally refers to any simulated environment (e.g., three-dimensional (3D) or two-dimensional (2D)) that is displayed by an ER system.

Scene 405 includes a portion of the real world, as shown by real world content 410. Additionally, scene 405 includes a hologram 415 (aka stimulus). In this particular scenario, the user is able to observe both the real world content 410 and the hologram 415. As a result, HMD 400 is either one of an AR or MR system. In other scenarios, HMD 400 may be a VR system.

Figure 5:
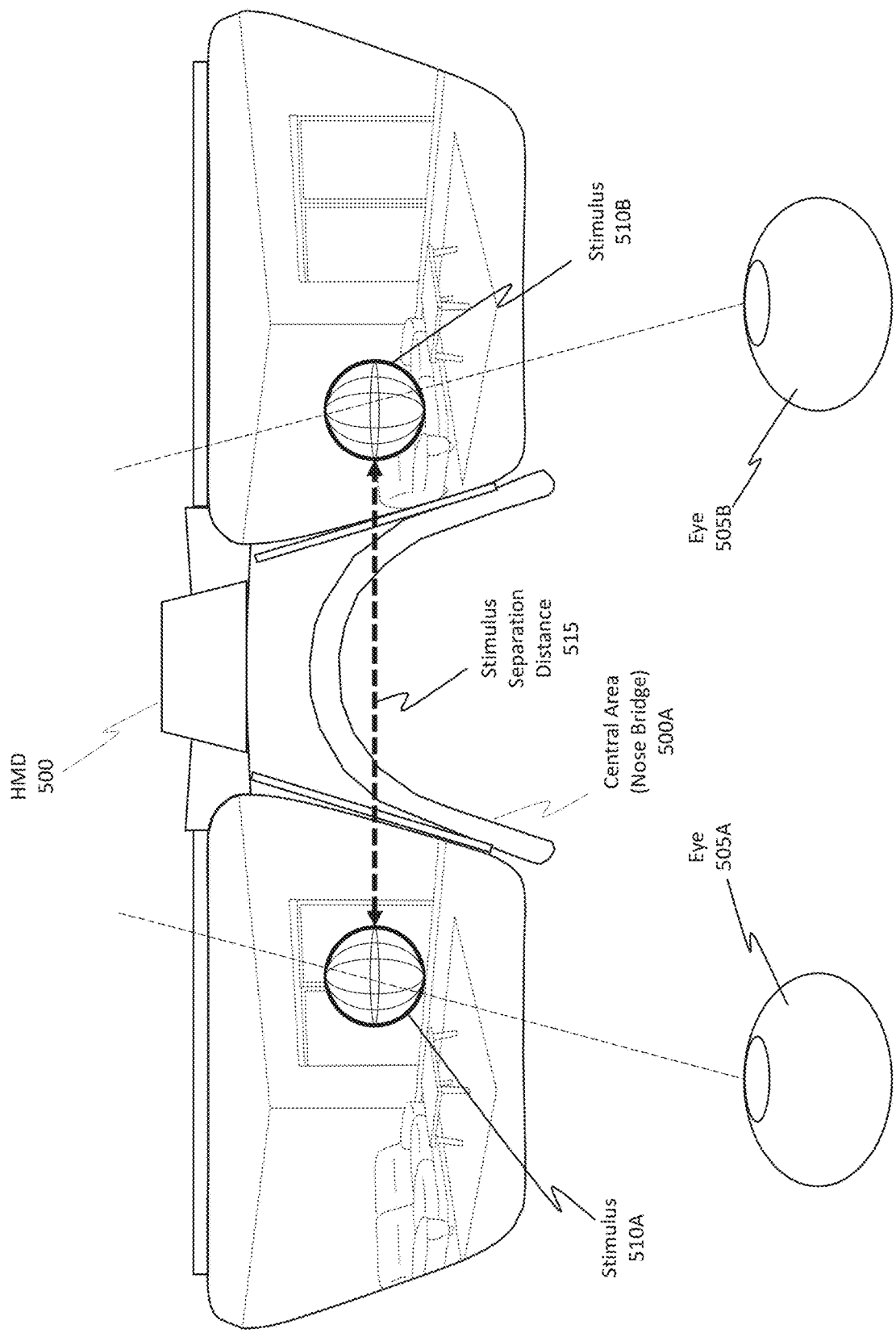
FIG. 5 illustrates a scenario in which stimuli are being displayed.

FIG. 5 shows an HMD 500, which corresponds to HMD 400 of FIG. 4. HMD 500 includes the lefthand display and the righthand display mentioned earlier. HMD 500 can also optionally include a nose bridge or a central area 500A, which is the portion of the HMD 500 that rests on the user's nose. In some scenarios, HMD 500 may omit the nose bridge and instead simply have a central area or region of the HMD 500.

The user's left eye 505A will observe content displayed in the lefthand display. The user's right eye 505B will observe content in the righthand display.

In the example shown in FIG. 5, HMD 500 is rendering or displaying a first version of a stimulus 510A (which can also be referred to more generally as an "image") in the lefthand display. HMD 500 is displaying a second version of the stimulus 510B in the righthand display.

Stimulus 510A and 510B correspond to one another in that they represent the same hologram or virtual content. These stimuli might be positioned at different horizontal coordinates of the two displays to enable the user to perceive a depth for the resulting stimulus when the images are fused together in the user's mind. The user's mind will fuse the resulting content together, and that fusion will enable the user to view the stimulus at a particular depth in the scene.

By way of further clarification, HMD 500 displays stimulus 510A at a first horizontal position with respect to the HMD's lefthand display, and HMD 500 displays stimulus 510B at a second horizontal position with respect to the HMD's righthand display. The distance between those two horizontal positions is referred to as the stimulus separation distance 515.

Notice, in FIG. 5, the stimulus separation distance 515 is initially set to a value that is definitively lower than the user's IPD, even though the user's IPD may not be known at this point in time. That is, the distance between stimulus 510A and stimulus 510B is currently set to be significantly smaller than an average user's IPD, as shown by the dashed, angled lines in FIG. 5. Each dashed, angled line passes through the user's pupils and through the corresponding stimulus. Notice, stimulus 510A is not directly in line with the user's left pupil; rather, stimulus 510A is at a position that is relatively proximate to the central area 500A. Similarly, stimulus 510B is not directly in line with the user's right pupil; rather, stimulus 510B is at a position that is relatively proximate to the central area 500A. Thus, the stimulus separation distance 515, in FIG. 5, is set to a value that is smaller than the user's IPD and is smaller than the average user's IPD. Typically, the value for this initial stimulus separation distance 515 is set to around 40 millimeters (mm), which is significantly smaller than the average user's IPD.

Figure 6:
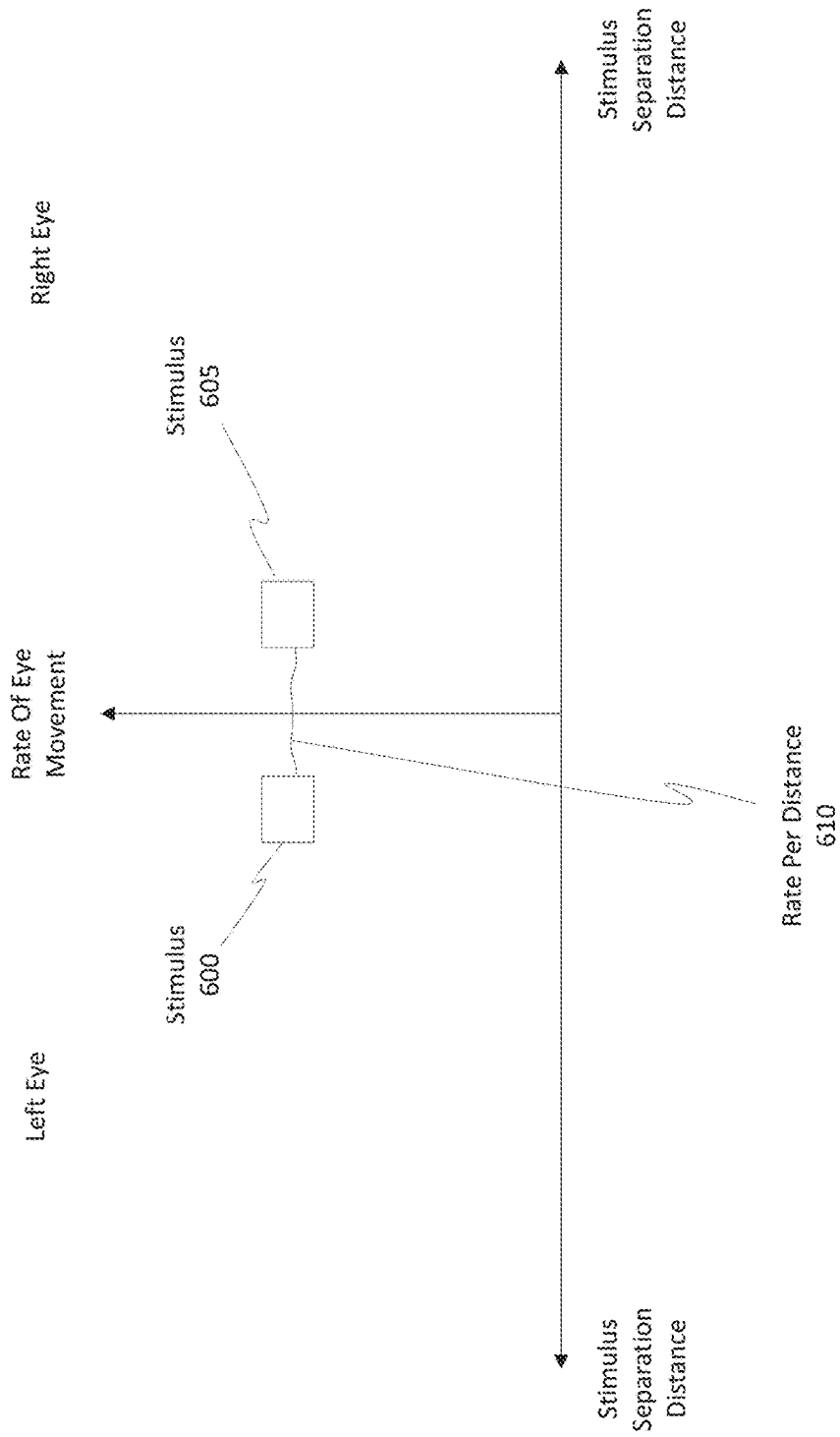
FIG. 6 illustrates a plot of a user's rate of eye movement.

In accordance with the disclosed principles, service 110 of FIG. 1 causes stimulus 510A and 510B to be displayed. To determine the user's IPD, service 110 progressively increases the stimulus separation distance 515 by progressively moving, in opposing horizontal directions relative to one another, stimulus 510A and stimulus 510B. While stimulus separation distance 515 is being progressively increased by progressively moving stimulus 510A and stimulus 510B, service 110 tracks one or perhaps both of the user's eyes to detect the interruption mentioned earlier. FIG. 6 is illustrative.

FIG. 6 shows a chart or plot. The rectangle labeled stimulus 600 corresponds to stimulus 510A of FIG. 5, and the rectangle labeled stimulus 605 corresponds to stimulus 510B. The "Y" axis is the measured rate of eye movement, and the "X" axis is the stimulus separation distance. The eye trackers mentioned earlier are able to track the user's eyes while the stimuli are being manipulated, and the data from those eye trackers is shown in the plot of FIG. 6. The intersection of the "X" and "Y" axes corresponds to an initial, minimum value for the stimulus separation distance. Typically, that minimum value is around 40 millimeters (mm), meaning that 40 mm is the initial distance between stimulus 510A in FIG. 5 and stimulus 510B. Service 110 is designed to progressively increase the stimulus separation distance through a range of values until a detectable event or interruption happens with respect to the rate of eye movement. That is, as shown in FIG. 6, while the stimulus separation distance is progressively increased, the rate of eye movement is relatively stable or smooth, with no sudden peaks or values.

Once the stimuli are displayed at positions where the user's eyes would have to diverge or point outwardly (i.e. the opposite of being cross eyed), then a detectable phenomenon happens in which the user's eyes experience an event similar to a bounce. Stated differently, the rate of eye movement is no longer smooth; instead, there is a significant and detectable jitter or shift in the rate of eye movement. The point at which that shift in the rate of eye movement occurs can be recorded and used as a baseline for the user's IPD because it was at that point that the user's eyes had to diverge in order to view the two stimuli. Accordingly, FIG. 6 shows a scenario where the plotted rate per distance 610 is still relatively smooth, meaning that the stimulus separation distance has not met or exceeded the user's IPD.

Figure 7:
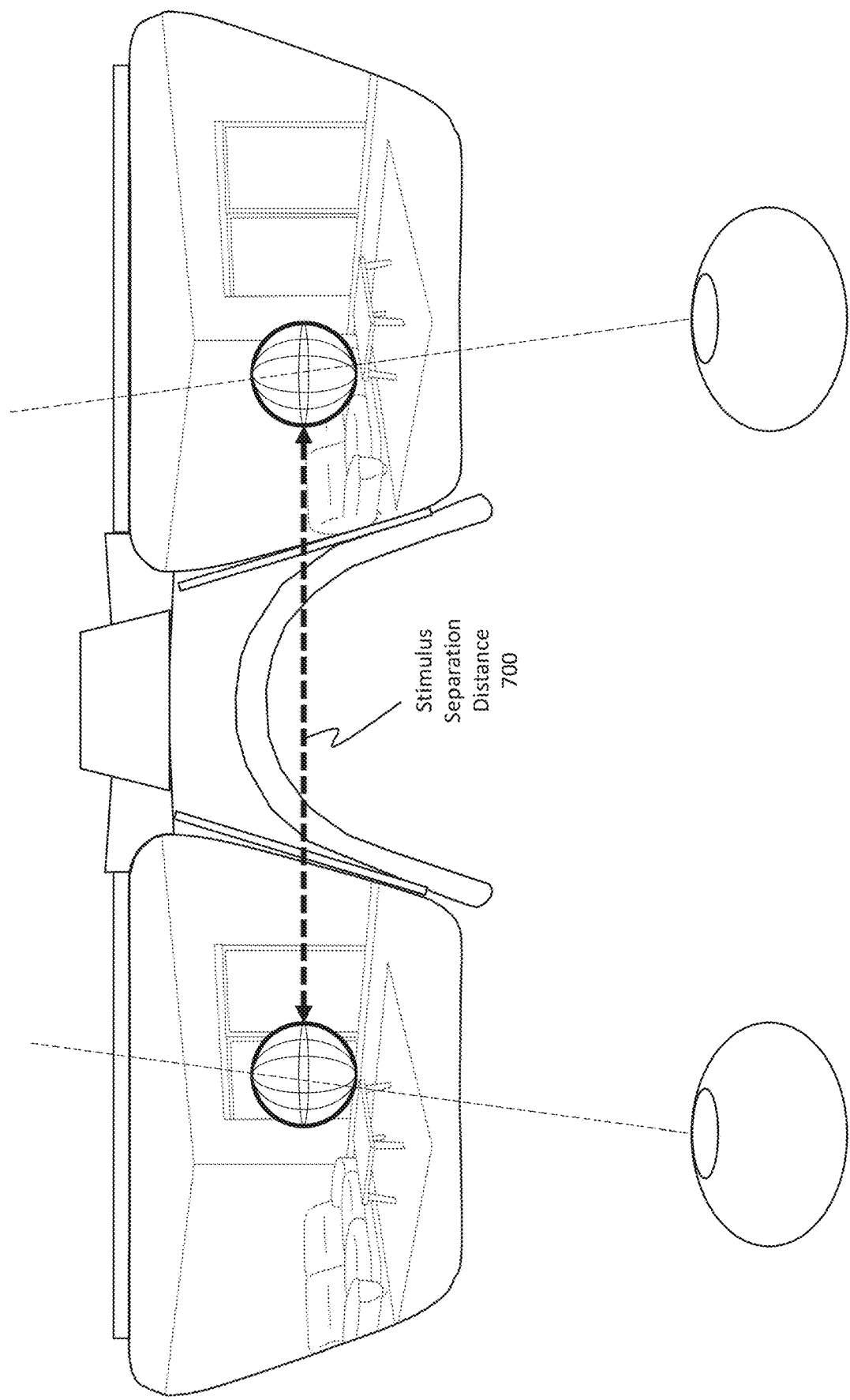
FIG. 7 illustrates a scenario in which stimuli are being displayed.
Figure 8:
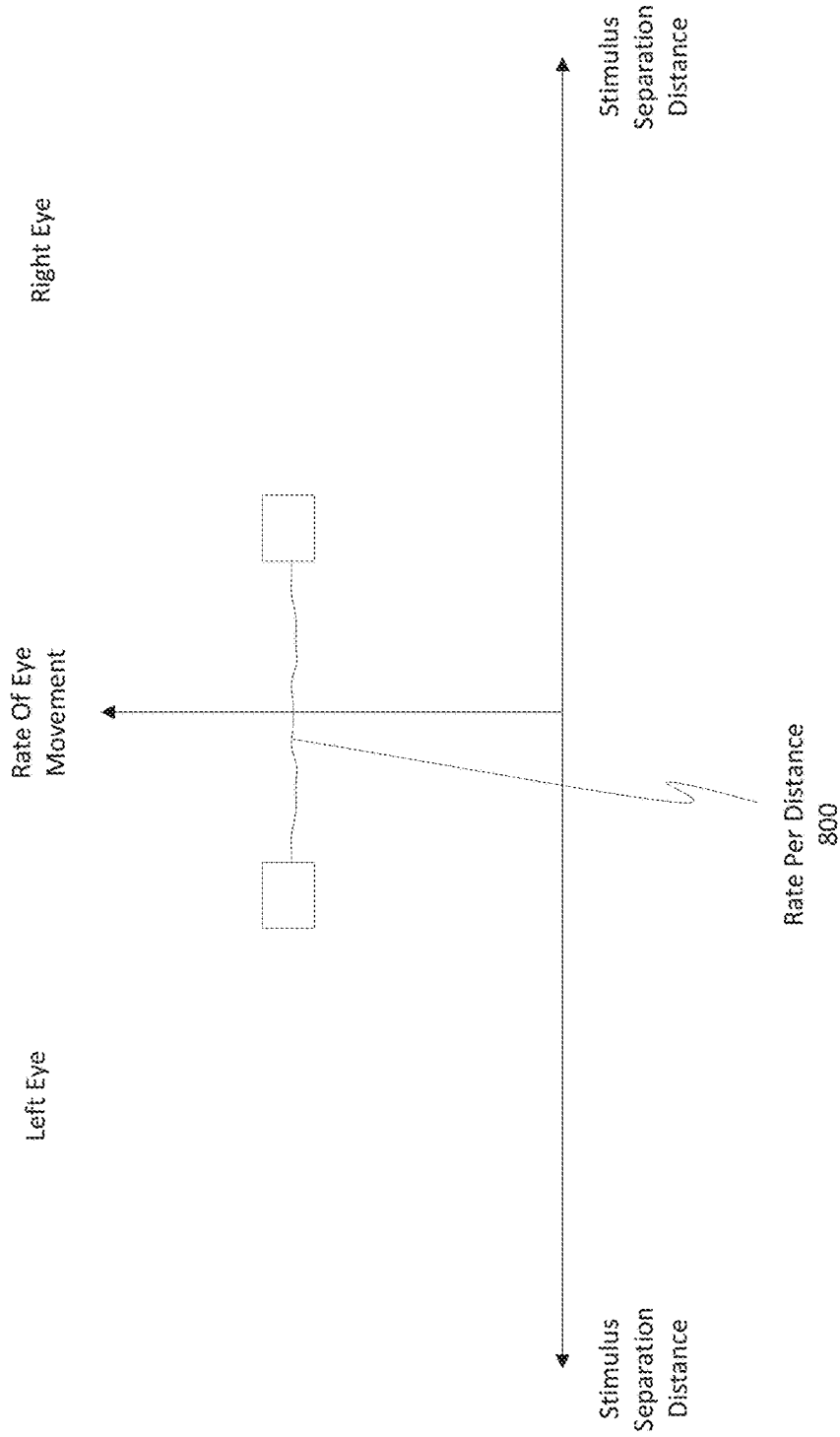
FIG. 8 illustrates a plot of a user's rate of eye movement.

FIG. 7 shows a scenario where the stimulus separation distance 700 has been progressively increased as compared to stimulus separation distance 515 of FIG. 5. Similarly, FIG. 8 shows how the rate per distance 800 is still relatively stable or constant. Notice, in FIG. 8, more plot data is provided as compared to the plot data shown in FIG. 6 due to the fact that the two stimuli are being progressively moved and the user's eyes are being tracked.

Figure 9:
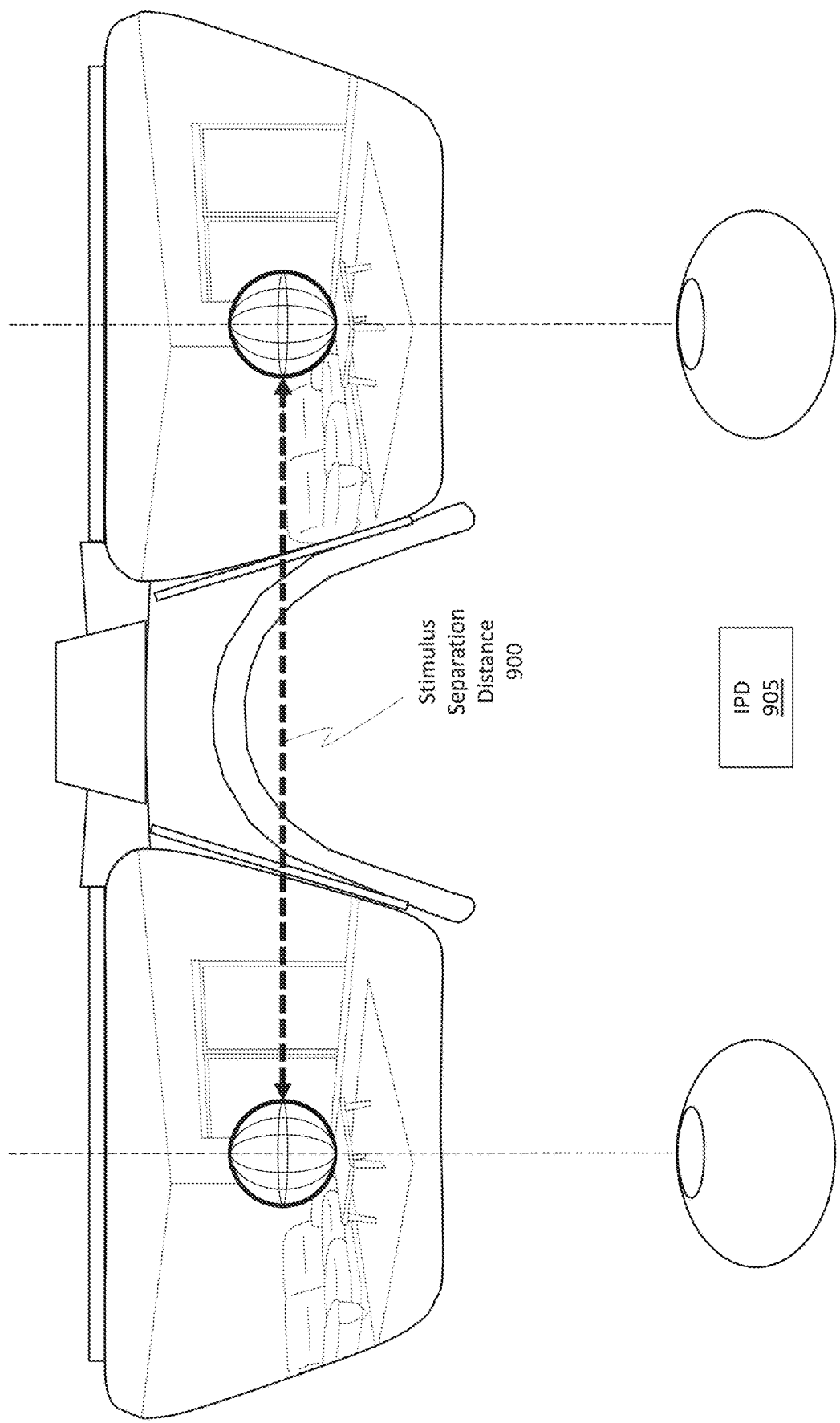
FIG. 9 illustrates a scenario in which stimuli are being displayed.
Figure 10:
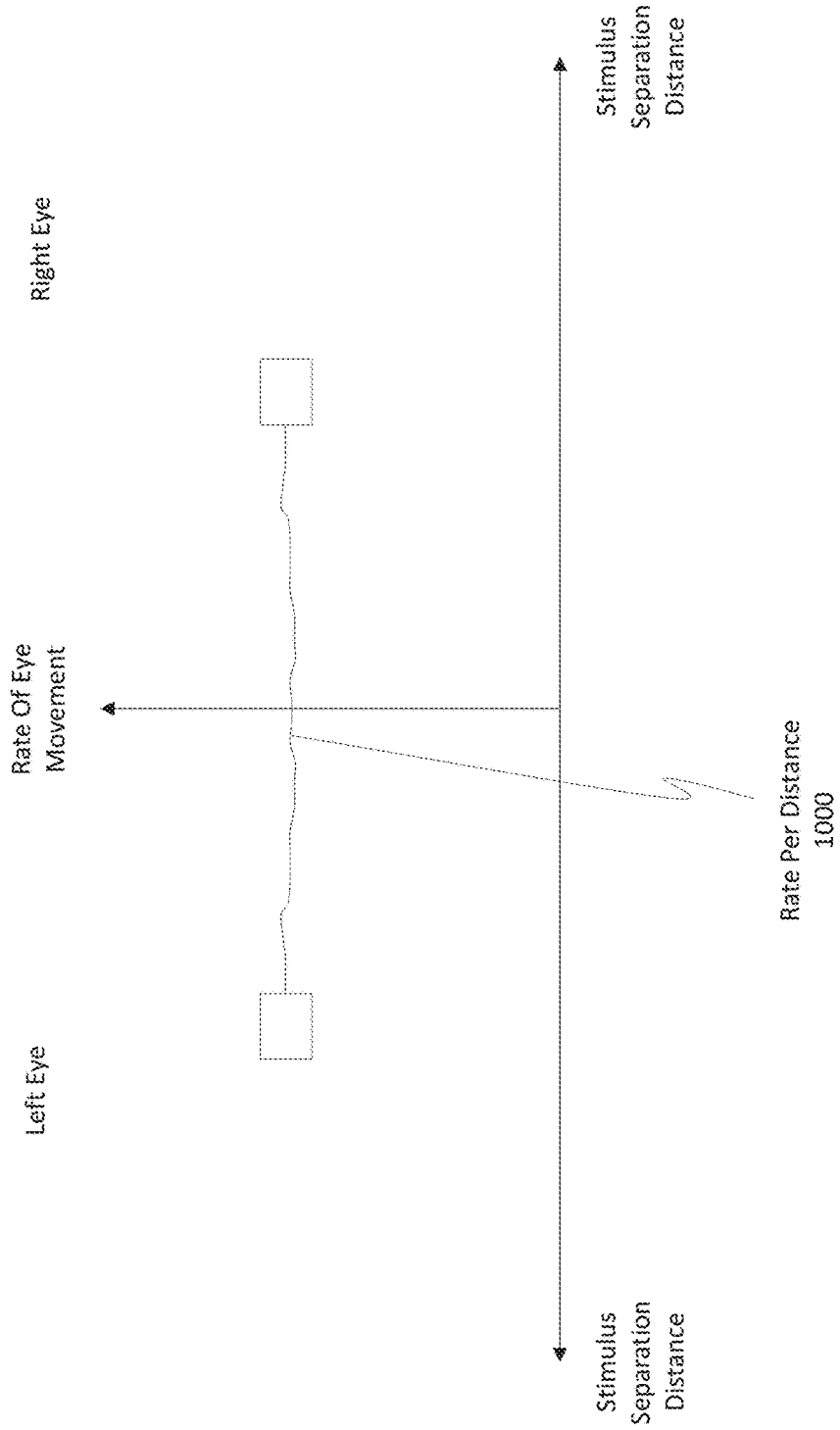
FIG. 10 illustrates a plot of a user's rate of eye movement.

FIG. 9 shows a scenario where the stimulus separation distance 900 has been progressively increased as compared to the stimulus separation distance 700 of FIG. 7. In this particular scenario, the stimulus separation distance 900 now matches the user's IPD 905, as reflected by the straight, dashed, and vertical lines extending from each user's pupil to each corresponding stimulus. Similarly, FIG. 10 shows how the rate per distance 1000 is still relatively stable or constant. Notice, in FIG. 10, more plot data is provided as compared to the plot data shown in FIG. 8 due to the fact that the two stimuli are being progressively moved and the user's eyes are being tracked.

Figure 11:
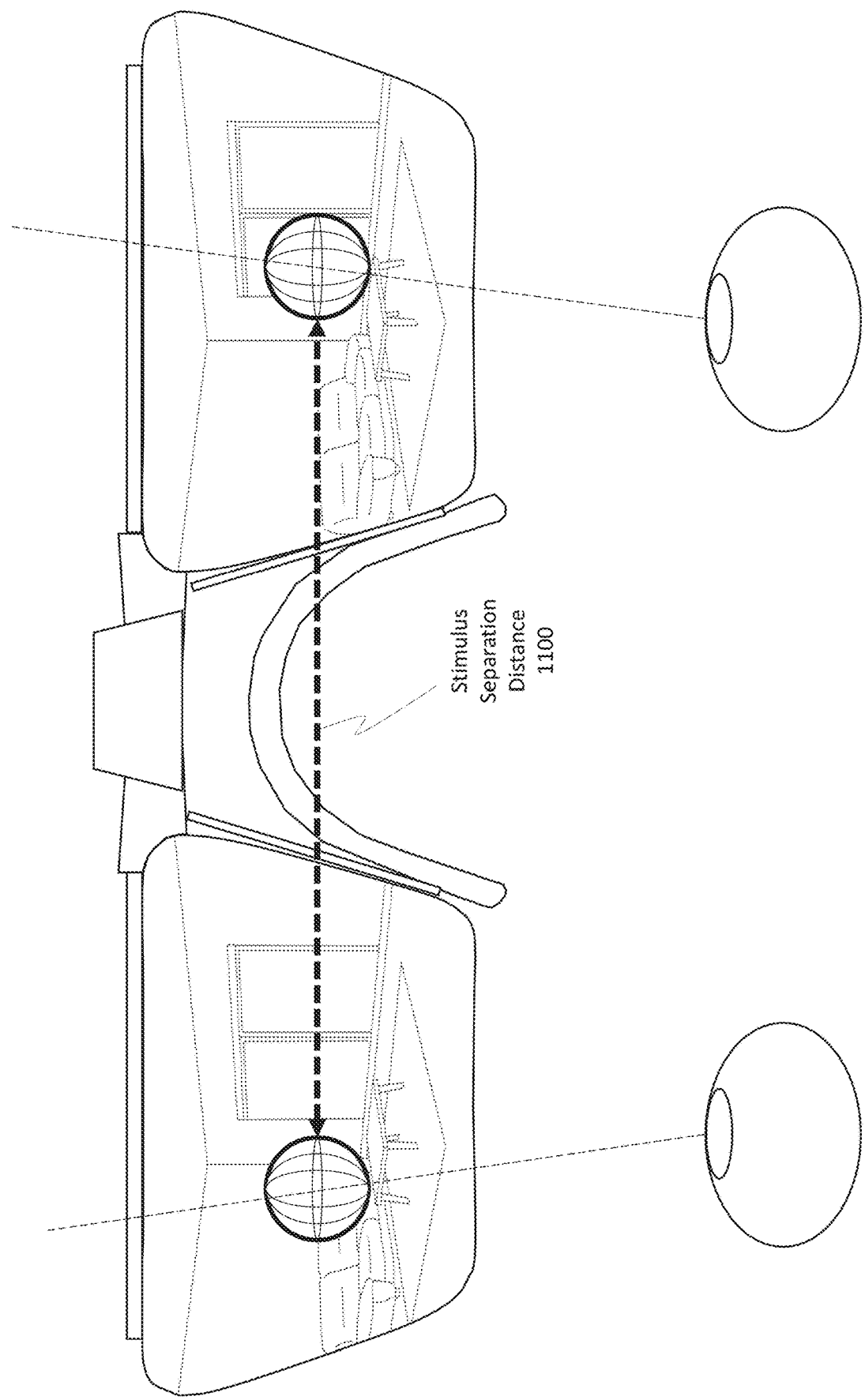
FIG. 11 illustrates a scenario in which stimuli are being displayed.

As was shown in FIG. 9, service 110 from FIG. 1 progressively increased the stimulus separation distance up to the user's IPD. At this point, it is still unknown what the user's IPD actually is, so service 110 will continue to progressively increase the stimulus separation distance. FIG. 11 is illustrative.

Figure 12:
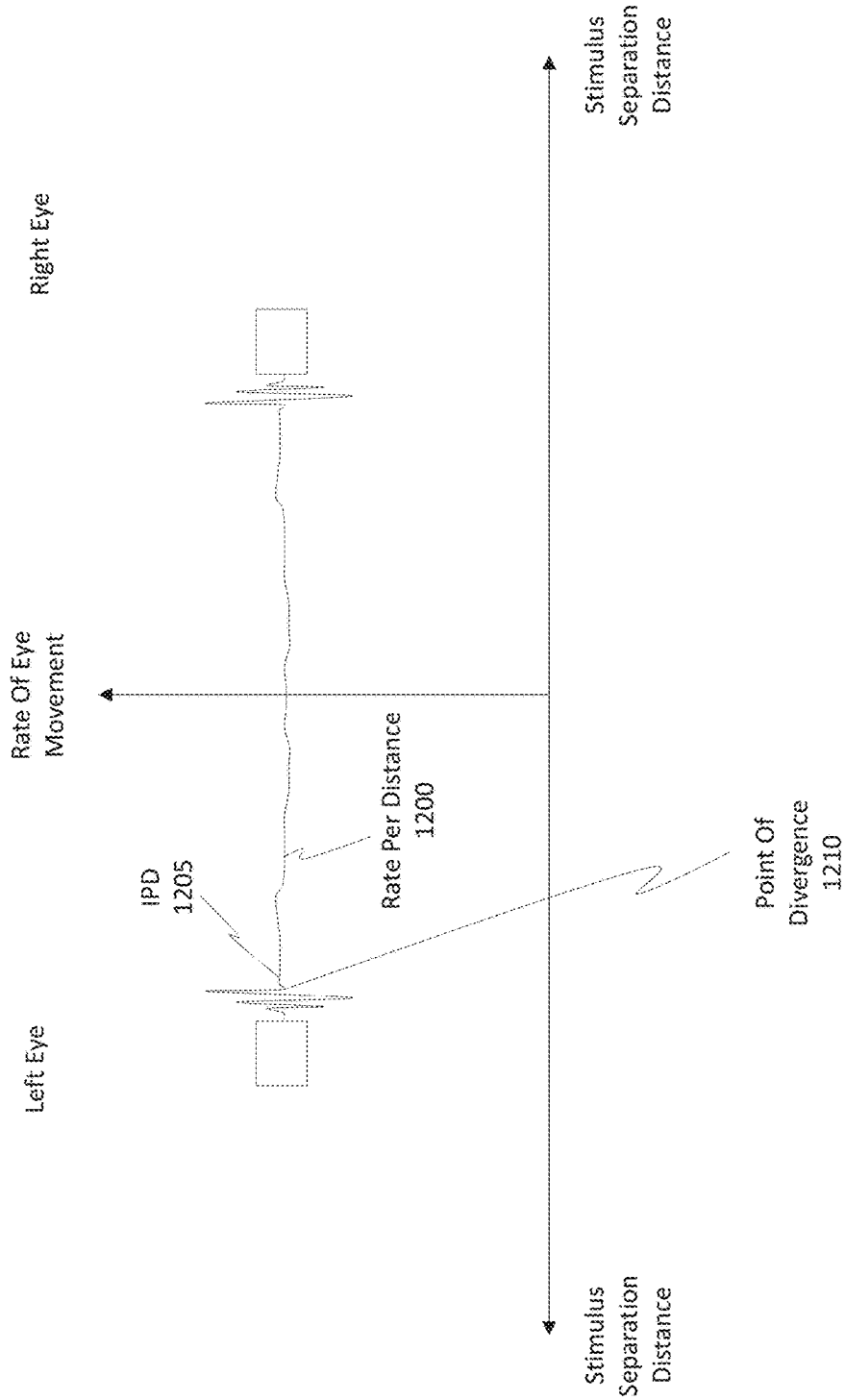
FIG. 12 illustrates a plot of a user's rate of eye movement.

FIG. 11 shows a scenario where the stimulus separation distance 1100 has been progressively increased as compared to the stimulus separation distance 900 of FIG. 9. In this particular scenario, the stimulus separation distance 1100 now exceeds the user's IPD, as reflected by the outwardly angled, dashed lines extending from each user's pupil to each corresponding stimulus. Similarly, FIG. 12 shows the rate per distance 1200. Notice, at the point where the stimulus separation distance exceeded the user's IPD, the plotted data is no longer stable or relatively constant.

To illustrate, with respect to the plot provided for the user's left eye in FIG. 12 and starting at the intersection of the "Y" and "X" axes, the rate per distance 1200 is smooth until reaching the user's IPD 1205. After the stimulus separation distance exceeds the IPD 1205, the user's eyes have to diverge, as shown by the point of divergence 1210. The result of the user's eyes diverging is that the plot for the rate per distance 1200 is shown as being erratic or bouncing, including multiple high peaks and low valleys. These plot "bounces" are detectable and can be used to determine the user's IPD 1205.

Returning back to FIG. 1, service 110 is thus tasked with progressively increasing the stimulus separation distance 120 that exists between two stimuli. Service 110 monitors the rate of eye movement of one or both of the user's eyes. When the rate of eye movement is detected as exceeding a predefined threshold or as varying from a recognizable pattern, then service 110 will recognize that the stimulus separation distance 120 has exceeded the user's IPD 115. Service 110 may then determine what the user's IPD 115 is based on when the variance or change in the user's rate of eye movement occurred.

Example Methods

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 13:
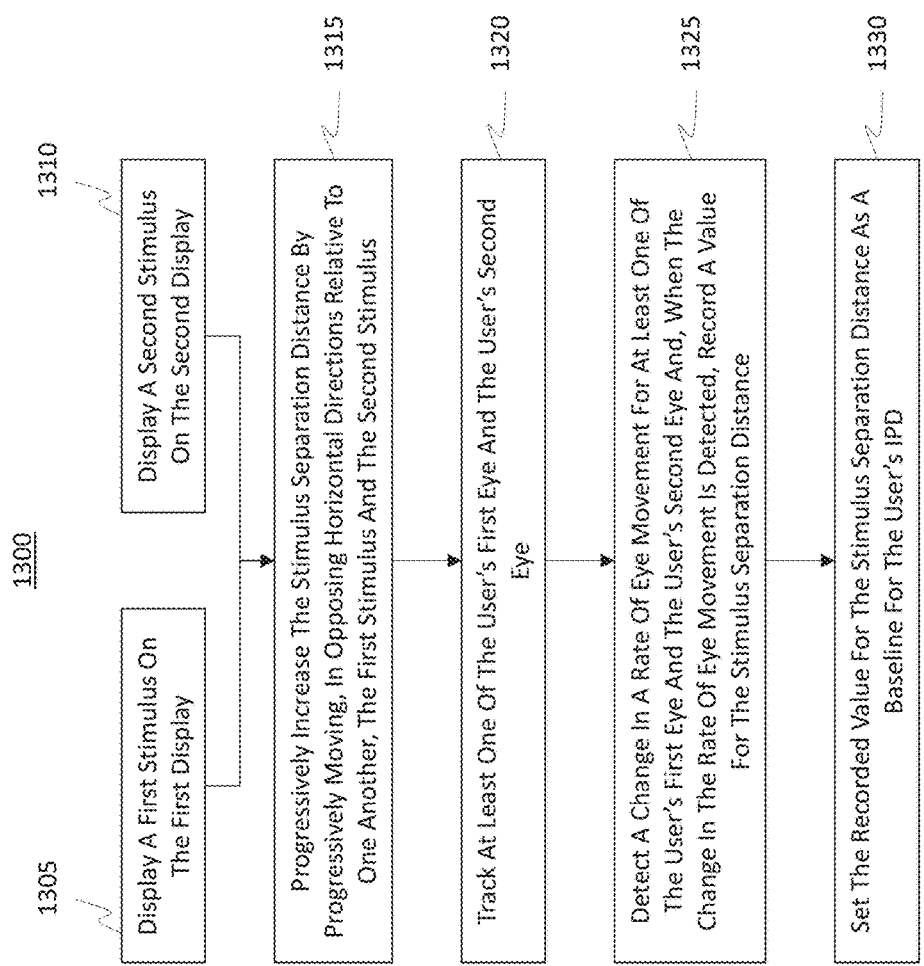
FIG. 13 illustrates a flowchart of an example method for determining a user's IPD.

Attention will now be directed to FIG. 13, which illustrates a flowchart of an example method 1300 for determining an IPD of a user. Method 1300 may be implemented within architecture 100 of FIG. 1. Furthermore, method 1300 may be implemented by service 110 of FIG. 1 or, more generally, by any type of computing system, including ER system 105 of FIG. 1. The computer system may include a first display and a second display. Optionally, the first display and the second display are separate display units on an HMD. In some scenarios, the first display and the second display are included in a same display unit on the HMD.

Method 1300 includes an act (act 1305) of displaying a first stimulus on the first display. The first stimulus is visible to a first eye of the user. Stimulus 510A of FIG. 5 is one example of this first stimulus.

In parallel with act 1305, act 1310 includes displaying a second stimulus on the second display. The second stimulus is visible to a second eye of the user. Stimulus 510B of FIG. 5 is one example of this second stimulus. The first stimulus and the second stimulus are different versions of a particular stimulus that is being displayed. For instance, with reference to FIG. 5, both stimulus 510A and stimulus 510B represent a sphere.

A stimulus separation distance is a distance that exists between the first stimulus and the second stimulus. For example, stimulus separation distance 515 of FIG. 5 is the distance between stimulus 510A and stimulus 510B. In some scenarios, the stimulus separation distance, prior to being progressively increased, is set to a value of about 40 millimeters. In some scenarios, the stimulus separation distance, prior to being progressively increased, is set to a value that is less than about 54 millimeters (i.e. the lower end of an average adult user's IPD). In some implementations, the value is set to be some percentage value less than the lower end of the average adult user's IPD, such as 10% less, 20% less, or 30% less.

Act 1315 includes progressively increasing the stimulus separation distance. This increase is achieved by progressively moving, in opposing horizontal directions relative to one another, the first stimulus and the second stimulus. For example, FIGS. 7, 9, and 11 showed how the two stimuli were progressively moved outward relative to the HMD's nose guard or, in other words, the stimuli were moved toward outer end regions of the HMD's displays.

Progressively increasing the stimulus separation distance is completed within a time period of less than about 5 seconds. In some scenarios, the increase is performed in less than 4 seconds, less than 3 seconds, less than 2 seconds, or perhaps even less than 1 second. In some extreme scenarios, the increase may take as long as 10 seconds. That being said, the increase is performed in 10 seconds or less.

The stimulus separation distance is permitted to be progressively increased up to a value that exceeds the upper end of the average adult user's IPD (e.g., about 68 mm). Sometimes, the distance is permitted to be increased to a value of about 75 millimeters. Notably, however, the value 75 mm may never be reached because the embodiments will typically stop the progressive increase once the user's IPD is determined, or rather, once the detected event or interruption is detected, which will occur before the distance reaches 75 mm. Thus, 75 mm may be a maximum value, and it may be the case that this maximum value is not reached. Instead, the progressive increase will stop whenever the user's IPD is determined, and that IPD value will likely be less than 75 mm.

For instance, if the starting value for the stimulus separation distance is 40 mm, then the stimulus separation distance is progressively increased through a range of values spanning 40 mm to 75 mm. In some implementations, the progressive increase involves discrete stepwise increments in the distance, analogous to a digital stepwise increase. For instance, the stimulus separation distance may be discretely increased by a value of 1 mm for each step, or perhaps by 0.1 mm, 0.2 mm, 0.3 mm, 0.4 mm, 0.5 mm, 0.6 mm. 0.7 mm, 0.8 mm, or 0.9 mm for each stepwise increase. The stimulus separation distance may be discretely increased by larger values as well, such as perhaps by 2 mm, 3 mm, and so on. Larger discrete steps are less optimal because it results in a less accurate determination for the user's IPD.

In other scenarios, the progressive increase involves a continuous increase. This type of increase may be thought of as being analogous to an analog increase that does not include discrete steps but that rather includes a progressive and continual increase.

In any event, progressively increasing the stimulus separation distance results in both the first stimulus and the second stimulus moving farther away from a nose bridge associated with the first display and with the second display, or moving farther away from a central region of the HMD. Thus, the two stimuli are being moved to locations that are closer to outer edges of the displays as opposed to inner edges of the displays.

While the stimulus separation distance is being progressively increased by progressively moving the first stimulus and the second stimulus, act 1320 includes tracking at least one of the user's first eye and the user's second eye. In some implementations, only one of the first or second eyes is tracked. In some implementations, both the first and second eyes are tracked. This tracking is performed by an eye tracker. Often, this eye tracker is a low end eye tracker, such as a low resolution eye tracker or some other type of simplified eye tracker.

While the stimulus separation distance is being progressively increased, act 1325 includes detecting a change in a rate of eye movement for at least one of the user's first eye and the user's second eye. Act 1325 further includes recording, when the change in the rate of eye movement is detected, a value for the stimulus separation distance.

The detected change in the rate of eye movement is determined to exceed a permitted threshold for changes to the rate of eye movement. For instance, this threshold may be set to allow for some minor fluctuations, such as fluctuations up to about 10% of the signal. By providing this threshold or buffer, the embodiments can avoid a false positive in identifying the user's IPD.

By way of further clarification, prior to detecting a threshold change in the rate of the eye movement, the rate of eye movement is approximately constant, or is at least within the defined buffer that accommodates fluctuations. In some scenarios, while the stimulus separation distance is being progressively increased and before the change in the rate of eye movement is detected, the rate of eye movement corresponds to an approximately linear plot line.

With the interruption now being detected in act 1325, act 1330 includes setting the recorded value for the stimulus separation distance as a baseline or parameter for the user's IPD. Stated differently, the recorded value is set as the render camera separation for the rendering cameras that are supposed to be positioned in aligned positions with respect to the user's pupils. Typically, the recorded value for the stimulus separation distance will be within a range spanning an average IPD for a human adult, where the average is between about 54 mm and about 68 mm. For users who have abnormal IPDs, their IPDs will also be recorded because the embodiments passed the stimuli through a separation distance range that far exceeded a human's IPD. For instance, in some extreme cases, the recorded value for the stimulus separation distance may be within a range spanning between about 48 mm and about 73 mm, despite the average adult human's IPD being only between 54 mm to 68 mm.

In some scenarios, the value that is recorded for the stimulus separation distance is less than the stimulus separation distance that is measured when the detected change in the rate of eye movement occurs. For example, FIG. 12 shows a scenario where the user's actual IPD 1205 is some minimal value that is less than the stimulus separation distance that is identified when the point of divergence 1210 occurs. Often, this minimal value is less than 1 mm, such as 0.75 mm, 0.5 mm, 0.25 mm 0.1 mm, or some value between 1 mm and 0.1 mm. Thus, the actual recorded value is less than the value determined when the point of divergence 1210 in FIG. 12 is identified.

In some implementations, method 1300 may further include an act of reducing the baseline for the user's IPD by a selected value. For example, the selected value for reducing the baseline may be between about 10% of the baseline to about 40% of the baseline. Thus, in some scenarios, the baseline is further reduced to a value that is between about 90% of the original baseline to about 60%, or perhaps 70%, of the original baseline.

Additional Features

Some embodiments are configured to display the stimuli at a set distance corresponding to a so-called "infinite" distance. With respect to depth operations performed by an HMD, it is generally acceptable to classify depths (relative to the HMD) over about 3 meters as being an "infinite" depth. In some scenarios, that value can be slightly smaller, such as 2.5 meters. In any event, stimuli can be caused to be displayed at an infinite depth.

These embodiments can then progressively modify the render camera positions for the simulated cameras in an attempt to determine the user's IPD. Whereas previously, the embodiments progressively moved the stimuli, in some cases, the embodiments progressively move the render camera positions of the simulated cameras while keeping the stimuli at a fixed, infinite distance. The render camera positions can be set initially so that the render camera separation starts at about 40 mm and then is progressively increased up to a maximum of about 75 mm. The progressive increase occurs until the embodiments detect the eye bump, bounce, or interruption that was mentioned previously. The operations mentioned above (e.g., detecting an eye bounce and setting the IPD) may be equally applicable to these embodiments.

Accordingly, the disclosed embodiments improve how a user's IPD is determined. By determining the user's IPD, improvements in user comfort and image display can also be realized.

Example Computer/Computer Systems

Figure 14:
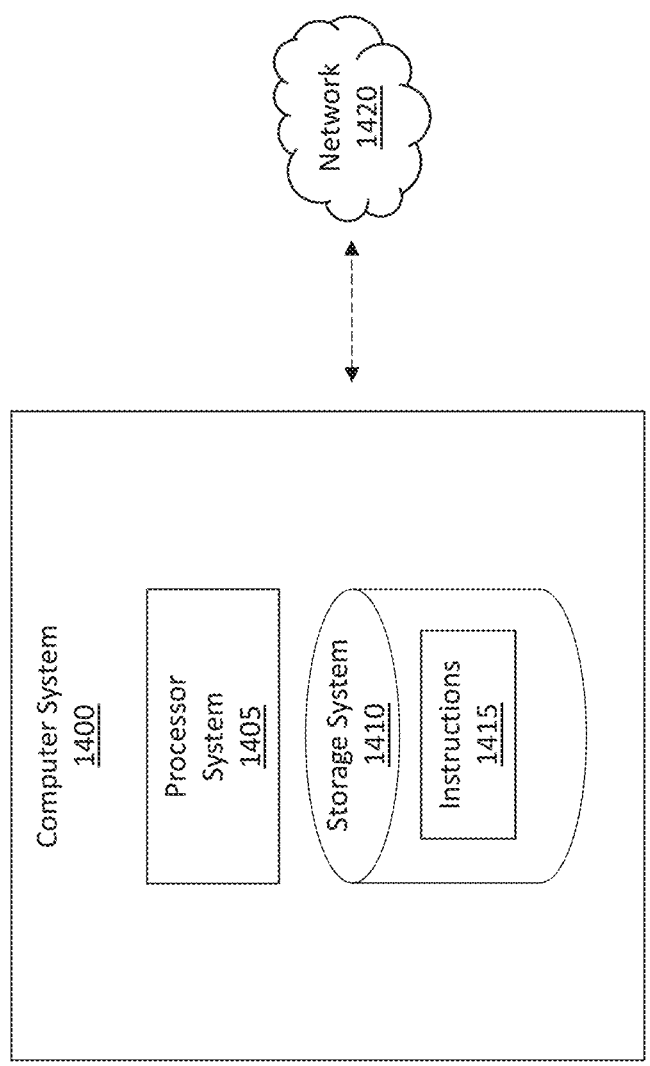
FIG. 14 illustrates an example computer system that can be configured to perform any of the disclosed operations.

Attention will now be directed to FIG. 14 which illustrates an example computer system 1400 that may include and/or be used to perform any of the operations described herein. Computer system 1400 may take various different forms. For example, computer system 1400 may be embodied as a tablet, a desktop, a laptop, a mobile device, or a standalone device, such as those described throughout this disclosure. Computer system 1400 may also be a distributed system that includes one or more connected computing components/devices that are in communication with computer system 1400. Computer system 1400 can be implemented as the ER system 105 of FIG. 1. In some cases, computer system 1400 can also implement service 110.

In its most basic configuration, computer system 1400 includes various different components. FIG. 14 shows that computer system 1400 includes a processor system 1405 that includes one or more processor(s) (aka a "hardware processing unit") and a storage system 1410.

Regarding the processor(s) of the processor system 1405, it will be appreciated that the functionality described herein can be performed, at least in part, by one or more hardware logic components. For example, and without limitation, illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

As used herein, the terms "executable module," "executable component," "component," "module," "service," or "engine" can refer to hardware processing units or to software objects, routines, or methods that may be executed on computer system 1400. The different components, modules, engines, and services described herein may be implemented as objects or processors that execute on computer system 1400 (e.g. as separate threads).

Storage system 1410 may include physical system memory, which may be volatile, non-volatile, or some combination of the two. The term "memory" may also be used herein to refer to non-volatile mass storage such as physical storage media. If computer system 1400 is distributed, the processing, memory, and/or storage capability may be distributed as well.

Storage system 1410 is shown as including executable instructions 1415. The executable instructions 1415 represent instructions that are executable by the processor(s) of processor system 1405 to perform the disclosed operations, such as those described in the various methods.

The disclosed embodiments may comprise or utilize a special-purpose or general-purpose computer including computer hardware, such as, for example, one or more processors and system memory, as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Furthermore, computer-readable storage media, which includes physical computer storage media and hardware storage devices, exclude signals, carrier waves, and propagating signals. On the other hand, computer-readable media that carry computer-executable instructions are "transmission media" and include signals, carrier waves, and propagating signals. Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 1400 may also be connected (via a wired or wireless connection) to external sensors (e.g., one or more remote cameras) or devices via a network 1420. For example, computer system 1400 can communicate with any number devices or cloud services to obtain or process data. In some cases, network 1420 may itself be a cloud network. Furthermore, computer system 1400 may also be connected through one or more wired or wireless networks to remote/separate computer systems(s) that are configured to perform any of the processing described with regard to computer system 1400.

A "network," like network 1420, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 1400 will include one or more communication channels that are used to communicate with the network 1420. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system that determines an interpupillary distance (IPD) of a user, said computer system comprising:
 a first display;
 a second display;
 a processor system; and
 a storage system that stores instructions that are executable by the processor system to cause the computer system to:
  display a first stimulus on the first display, the first stimulus being visible to a first eye of the user;
  display a second stimulus on the second display, the second stimulus being visible to a second eye of the user, wherein a stimulus separation distance is a distance that exists between the first stimulus and the second stimulus;
  progressively increase the stimulus separation distance by progressively moving, in opposing horizontal directions relative to one another, the first stimulus and the second stimulus;
  while the stimulus separation distance is being progressively increased by progressively moving the first stimulus and the second stimulus, track at least one of the user's first eye and the user's second eye;
  while the stimulus separation distance is being progressively increased, detect a change in a rate of eye movement for at least one of the user's first eye and the user's second eye and, when the change in the rate of eye movement is detected, record a value for the stimulus separation distance; and set the recorded value for the stimulus separation distance as a baseline for the user's IPD.

2. The computer system of claim 1, wherein the first display and the second display are separate display units.

3. The computer system of claim 1, wherein the first display and the second display are included in a same display unit.

4. The computer system of claim 1, wherein the first stimulus and the second stimulus are different versions of a particular stimulus that is being displayed.

5. The computer system of claim 1, wherein the stimulus separation distance, prior to being progressively increased, is set to a value of about 40 millimeters.

6. The computer system of claim 1, wherein the stimulus separation distance, prior to being progressively increased, is set to a value that is less than about 54 millimeters.

7. The computer system of claim 1, wherein progressively increasing the stimulus separation distance is completed within a time period of less than about 5 seconds.

8. The computer system of claim 1, wherein the stimulus separation distance is permitted to be progressively increased up to a value of about 75 millimeters.

9. The computer system of claim 1, wherein the recorded value for the stimulus separation distance is within a range spanning an average IPD for a human adult.

10. The computer system of claim 1, wherein the recorded value for the stimulus separation distance is within a range spanning 48 millimeters to 73 millimeters.

11. A method for determining an interpupillary distance (IPD) of a user, said method comprising:
    displaying a first stimulus on a first display, the first stimulus being visible to a first eye of the user;
    displaying a second stimulus on a second display, the second stimulus being visible to a second eye of the user, wherein a stimulus separation distance is a distance that exists between the first stimulus and the second stimulus;
    progressively increasing the stimulus separation distance by progressively moving, in opposing directions relative to one another, the first stimulus and the second stimulus;
    while the stimulus separation distance is being progressively increased by progressively moving the first stimulus and the second stimulus, tracking at least one of the user's first eye and the user's second eye;
    while the stimulus separation distance is being progressively increased, detecting a change in a rate of eye movement for at least one of the user's first eye and the user's second eye and, when the change in the rate of eye movement is detected, recording a value for the stimulus separation distance; and
    setting the recorded value for the stimulus separation distance as a baseline for the user's IPD.

12. The method of claim 11, wherein the method further includes reducing the baseline for the user's IPD by a selected value, said selected value for reducing the baseline being between about 10% of the baseline to about 40% of the baseline.

13. The method of claim 11, wherein the baseline is further reduced to a value that is between about 90% of the baseline to about 70% of the baseline.

14. The method of claim 11, wherein progressively increasing the stimulus separation distance results in both the first stimulus and the second stimulus moving farther away from a nose bridge associated with the first display and with the second display.

15. The method of claim 11, wherein the detected change in the rate of eye movement is determined to exceed a threshold.

16. The method of claim 11, wherein, prior to detecting the change in the rate of eye movement, the rate of eye movement is approximately constant.

17. The method of claim 11, wherein, while the stimulus separation distance is being progressively increased and before the change in the rate of eye movement is detected, the rate of eye movement corresponds to an approximately linear plot line.

18. The method of claim 11, wherein the value that is recorded for the stimulus separation distance is less than the stimulus separation distance that is measured when the detected change in the rate of eye movement occurs.

19. A method for determining an interpupillary distance (IPD) of a user, said method comprising:
    displaying a first stimulus on a first display, the first stimulus being visible to a first eye of the user;
    displaying a second stimulus on a second display, the second stimulus being visible to a second eye of the user, wherein a stimulus separation distance is a distance that exists between the first stimulus and the second stimulus;
    progressively increasing the stimulus separation distance by progressively moving, in opposing directions relative to one another, the first stimulus and the second stimulus;
    while the stimulus separation distance is being progressively increased by progressively moving the first stimulus and the second stimulus, tracking the user's first eye;
    while the stimulus separation distance is being progressively increased, detecting a change in a rate of eye movement for the user's first eye and, when the change in the rate of eye movement is detected, recording a value for the stimulus separation distance; and
    setting the recorded value for the stimulus separation distance as a baseline for the user's IPD.

20. The method of claim 19, wherein the stimulus separation distance, prior to being progressively increased, is set to a value that is less than 54 millimeters.

* * * * *